United States Patent [19]

Hirata et al.

[11] Patent Number: 4,618,687

[45] Date of Patent: Oct. 21, 1986

[54] CYCLOPENTENONE COMPOUND AND PROCESS FOR PRODUCTION THEREOF

[75] Inventors: Tadashi Hirata, Yokohama; Hiromitsu Saito, Sagamihara; Makoto Morimoto, Shizuoka, all of Japan

[73] Assignee: Kyowa Hakko Kogyo Co., Ltd., Tokyo, Japan

[21] Appl. No.: 724,549

[22] Filed: Apr. 18, 1985

[30] Foreign Application Priority Data

Apr. 23, 1984 [JP] Japan .................................. 59-81500

[51] Int. Cl.⁴ .......................................... C07D 311/94
[52] U.S. Cl. .................................. 549/396; 568/379; 564/189
[58] Field of Search ...................... 549/396; 568/379

[56] References Cited

U.S. PATENT DOCUMENTS 4,401,825  8/1983  Weinges et al. .................... 549/396

Primary Examiner—Nicky Chan
Attorney, Agent, or Firm—Fitzpatrick, Cella, Harper & Scinto

[57] ABSTRACT

A cyclopentenone compound represented by the following formula:

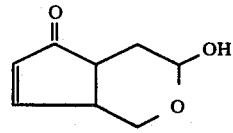

has an antitumor effect and can be produced from the antibiotic XK-213.

1 Claim, No Drawings

CYCLOPENTENONE COMPOUND AND PROCESS FOR PRODUCTION THEREOF

BACKGROUND OF THE INVENTION

This invention relates to a cyclopentenone compound represented by the following formula (I):

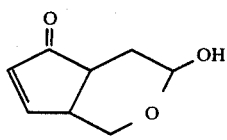

[which will be hereinafter referred to as compound (I), and compounds with other formulae will also be referred to in the similar manner] and to a process for producing compound (I) from antibiotic XK-213.

antibiotic XK-213 is an antitumor antibiotic produced by Actinomycetes and is disclosed in Japanese Published Unexamined patent application No. 59777/1981.

Compound (I) is a compound having a cytocidal effect on tumor cells.

DETAILED DESCRIPTION OF THE INVENTION

Compound (I) can be produced according to the following steps.

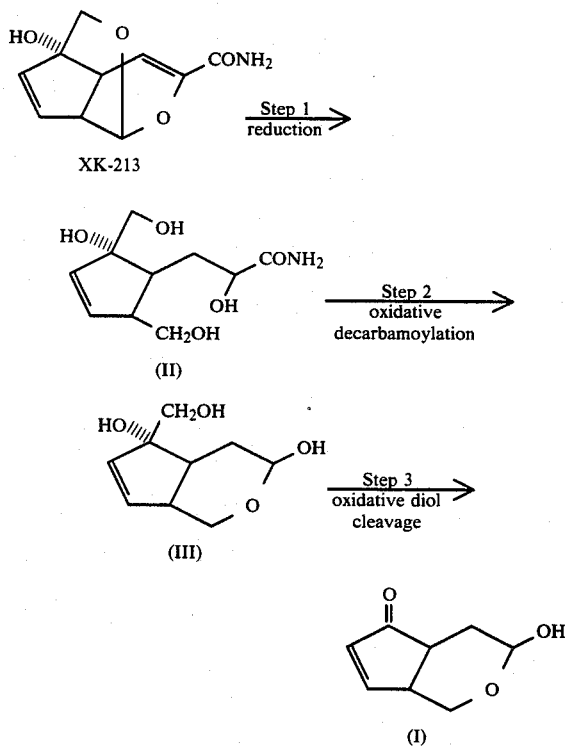

Namely, compound (I) can be produced by reducing XK-213 with a reducing agent, thereby obtaining compound (II), then oxidatively decarbamoyling the thus obtained compound, thereby obtaining compound (III), and further subjecting the thus obtained compound to oxidative diol cleavage reaction.

Any reducing agent can be used in the reduction reaction of step 1, so long as it reduces ester, aldehyde and ketone groups and does not reduce carbamoyl groups. Preferably, sodium borohydride is used. The solvent includes alcohols such as methanol, ethanol, etc., and solvent mixtures of water and alcohols, water and tetrahydrofuran, and water and dioxane, but the solvent to be used is not limited to these solvents. Reaction temperature is preferably in a range of $-20°$ to $50°$ C., but is not limited to this range.

Oxidative decarbamoylation reaction of step 2 is carried out in an aqueous solvent such as water-acetonitrile, water-acetone, water-alcohols, etc. at a reaction temperature of $-20°$ to $50°$ C., using calcium perchlorate as an oxidizing agent.

In the third step, an oxidative diol cleavage reaction is carried out, using an oxidizing agent capable of performing an oxidative cleavage reaction of the adjacent diol group, such as periodic acid and its salts, lead tetraacetate, etc. The reaction solvent is those usually used in such reactions, for example, water, alcohols (methanol, ethanol, etc.), halogenated hydrocarbons (methylene chloride, chloroform, carbon tetrachloride, etc.), esters (ethyl acetate, etc.), ethers (ethyl ether, dioxane, etc.), acetonitrile, etc. The reaction carried out at $-30°$ to $50°$ C.

Compound (I) can also exist as its tautomer (I'), and the present invention thus includes compound (I').

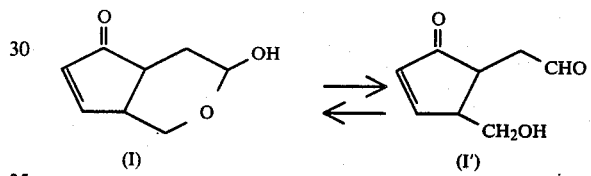

Certain specific embodiments of the invention are illustrated by the following examples.

EXAMPLE 1

(1-1) Preparation of 3-(1,4-dihydroxymethyl-2-cyclopenten-1-ol-5-yl)-2-hydroxypropanoic carboxamide (II)

At first, 300 mg of XK-213 is dissolved in 4.5 ml of water and 1.5 ml of methanol, and 152 mg of sodium borohydride is added thereto. The mixture is heated at $60°$ C. with stirring, and after 40 minutes, 100 mg of potassium carbonate is added thereto. The mixture is further heated with stirring for 50 minutes. After being left standing for cooling, the mixture is neutralized with 1N hydrochloric acid, concentrated and subjected to chromatographic purification (HP-20SS 70 ml, H$_2$O) to obtain 299 mg of compound (II) (96.2%).

PMR $\delta$ (D$_2$O) 6.11 (1H, m), 5.85 (1H, m), 4.24 (1H, m), 3.42–3.89 (4H, m), 3.01 (1H, m), 2.41 (1H, m), 1.63–2.14 (2H, m) $\nu_{max}$ (KBr) 1670

1-2) Preparation of 7-hydroxymethyl-3-oxabicyclo [4.3.0] nona-8-en-4,7-diol (III)

At first, 100 mg of compound (II) is dissolved in 3 ml of an aqueous 50% acetonitrile solution, and 126 mg of calcium hypochlorite is added thereto by portions. After the addition, the mixture is stirred at room temperature for 1 hour and 40 minutes. The reaction mixture is concentrated and chromatographically purified (HP-20SS 15 mg, H$_2$O) to obtain 52.8 mg of compound (III) (65.6%).

1-3) Preparation of 4-hydroxy-3-oxabicyclo [4.3.0]nona-8-en-7-on (I)

At first, 205 mg of compound (III) is dissolved in 3 ml of water, and 202 mg of periodic acid is added thereto. The mixture is stirred at room temperature for 1 hour and 30 minutes, and then chromatographically purified (HP-20SS 20 ml, water : methanol=4:1) to obtain 101 mg of compound (I) (59.5%).

PMR δ (CDCl3) 7.58 (dd, 1H, J=2.9, 5.9 Hz), 6.32 (dd, 1H, J=0.8, 5.9 Hz), 5.06 (dd, 1H, J=5.3, 8.4 Hz), 4.15 (dd, 1H, J=4.8, 12.1 Hz), 3.59 (dd, 1H, J=1.7, 12.1 Hz), 3.16 (ddddd, 1H, J=0.8, 1.7, 2.9, 4.8, 6.5 Hz), 2.55 (ddd, 1H, J=3.0, 6.1, 6.5 Hz), 2.49 (dd, 1H, J=3.0, 14.6 Hz), 1.83 (dd, 1H, J=6.1, 14.6 Hz)

CMR δ (D2O) 217.04, 170.13, 134.92, 91.24, 59.90, 42.87, 41.23, 28.68 m/e=154 (M+)

$\nu_{max}$ (KBr) 1685, 1695

EXAMPLE 2

Growth inhibitory effect on HeLa cells

Cultured HeLa S3 cells are suspended in an MEM medium (containing 10% bovine fetus serum and 6 mg/100 ml kanamycin) at a concentration of $5 \times 10^4$ cells/ml, 1 ml each of the cell suspension is pipetted in 24-hole multi-dishes, and the cells are cultured in a carbon dioxide cultivator with 5% $CO_2$ at 37° C. for 24 hours. Then, 0.1 ml each of drug solutions prepared at predetermined concentrations are added to each dish. Then, the cells are further cultured in the carbon dioxide cultivator for 96 hours. After the culturing, the culture liquor is removed from the dishes, and then 1 ml of PBS [physiological saline solution containing a phosphate buffer (pH 7.2)]is added to the dishes to gently wash the cell surfaces. Then, PBS is removed from the dishes. Then, 1 ml of PBS containing 0.05% trypsin and 0.02% EDTA is added to each dish. The dishes are left standing at room temperature for about 15 minutes. Adhered cells are peeled off, and 0.5 ml of the cell suspension is added to 10 ml of an isotonic solution. Cells are counted by a microcell counter to determine inhibition percent (%) against cell propagation of groups treated with the drug on the basis of the cell count of the control group. Linear expression showing a relationship between the concentration and the inhibition percent are obtained from the inhibition percent of the drug against the cell propagation at the respective concentration according to the least-squares method, and then the drug concentrations $IC_{50}$ showing a 50% inhibition against the cell propagation are obtained from the linear expression. The results are shown in Table 1.

TABLE 1

| Chemical | μg/ml | Cell count[a] Average ± standard deviation | Inhibition percent against cell propagation | $IC_{50}$ μg/ml |
|---|---|---|---|---|
| Control | — | 732 ± 24 | — | — |
| compound (I) | 10 | 7.1 ± 2.1 | 99.0 | 5.73 |
|  | 5 | 454 ± 21 | 38.0 |  |
|  | 3 | 784 ± 42 | −7.0 |  |
|  | 1 | 697 ± 58 | 4.8 |  |

[a] × 10³ cells/ml, result of three runs for each concentration.

What is claimed is:

1. A cyclopentenone compound represented by the following formula:

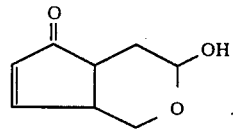

* * * * *